US010470796B2

(12) United States Patent
Page et al.

(10) Patent No.: US 10,470,796 B2
(45) Date of Patent: Nov. 12, 2019

(54) CANNULA WITH SENSORS TO MEASURE PATIENT BODYWALL FORCES

(71) Applicant: Intuitive Surgical Operations, Inc., Sunnyvale, CA (US)

(72) Inventors: Brett Page, Santa Clara, CA (US); Lawton N. Verner, San Jose, CA (US); John Ryan Steger, Sunnyvale, CA (US); Smita De, Palo Alto, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 306 days.

(21) Appl. No.: 15/329,982

(22) PCT Filed: Jul. 27, 2015

(86) PCT No.: PCT/US2015/042262
§ 371 (c)(1),
(2) Date: Jan. 27, 2017

(87) PCT Pub. No.: WO2016/018815
PCT Pub. Date: Feb. 4, 2016

(65) Prior Publication Data
US 2017/0265890 A1 Sep. 21, 2017

Related U.S. Application Data

(60) Provisional application No. 62/030,468, filed on Jul. 29, 2014.

(51) Int. Cl.
*A61B 1/32* (2006.01)
*A61B 17/34* (2006.01)
(Continued)

(52) U.S. Cl.
CPC ...... *A61B 17/3403* (2013.01); *A61B 17/0218* (2013.01); *A61B 17/34* (2013.01);
(Continued)

(58) Field of Classification Search
CPC combination set(s) only.
See application file for complete search history.

(56) References Cited

U.S. PATENT DOCUMENTS 5,599,348 A * 2/1997 Gentelia ............ A61B 17/3462
604/164.01
6,620,174 B2 9/2003 Jensen et al.
(Continued)

FOREIGN PATENT DOCUMENTS

| CN | 2772442 Y | 4/2006 |
| CN | 101528151 A | 9/2009 |

(Continued)

OTHER PUBLICATIONS

Extended European Search Report for Application No. EP15826885.4, dated Jan. 4, 2018, 4 pages.
(Continued)

*Primary Examiner* — Sameh R Boles
(74) *Attorney, Agent, or Firm* — Schwegman Lundberg & Woessner, P.A.

(57) ABSTRACT

A cannula is provided that includes a head portion that defines a proximal opening sized to receive one or more surgical instruments; an elongated inner tube rigidly fastened to the head portion defines an elongated conduit; a surgical instrument can be inserted within the conduit; an elongated overtube rigidly fastened to the head portion is coaxially aligned with the inner tube and extends about a portion of the inner tube; an inner wall of the overtube is spaced apart from an outer wall of the inner tube; sensors are disposed on the overtube to provide an indication of forces applied to the outer wall of the overtube in a direction generally transverse to the longitudinal dimension of the overtube.

20 Claims, 12 Drawing Sheets

(51) Int. Cl.
    *A61B 34/00*     (2016.01)
    *A61B 34/20*     (2016.01)
    *A61B 90/11*     (2016.01)
    *A61B 17/02*     (2006.01)
    *A61B 90/00*     (2016.01)
    *A61B 17/00*     (2006.01)

(52) U.S. Cl.
    CPC ...... *A61B 17/3417* (2013.01); *A61B 17/3421* (2013.01); *A61B 17/3423* (2013.01); *A61B 17/3494* (2013.01); *A61B 34/20* (2016.02); *A61B 34/70* (2016.02); *A61B 90/11* (2016.02); *A61B 2017/00862* (2013.01); *A61B 2034/2061* (2016.02); *A61B 2090/064* (2016.02); *A61B 2562/0261* (2013.01); *A61B 2562/046* (2013.01)

(56) References Cited

U.S. PATENT DOCUMENTS

| | | |
|---|---|---|
| 2006/0235314 A1 | 10/2006 | Migliuolo et al. |
| 2011/0178477 A1 | 7/2011 | Morel et al. |
| 2014/0137667 A1 | 5/2014 | Blumenkranz et al. |

FOREIGN PATENT DOCUMENTS

| | | |
|---|---|---|
| CN | 202105024 U | 1/2012 |
| EP | 1704822 A1 | 9/2006 |

OTHER PUBLICATIONS

International Search Report and Written Opinion for Application No. PCT/US2015/042262, dated Nov. 2, 2015, 11 pages.
International Preliminary Report on Patentability for Application No. PCT/US2015/042262, dated Feb. 9, 2017, 8 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Extended European Search Report for Application No. 19174165.1 dated Sep. 11, 2019, 8 pages.

\* cited by examiner

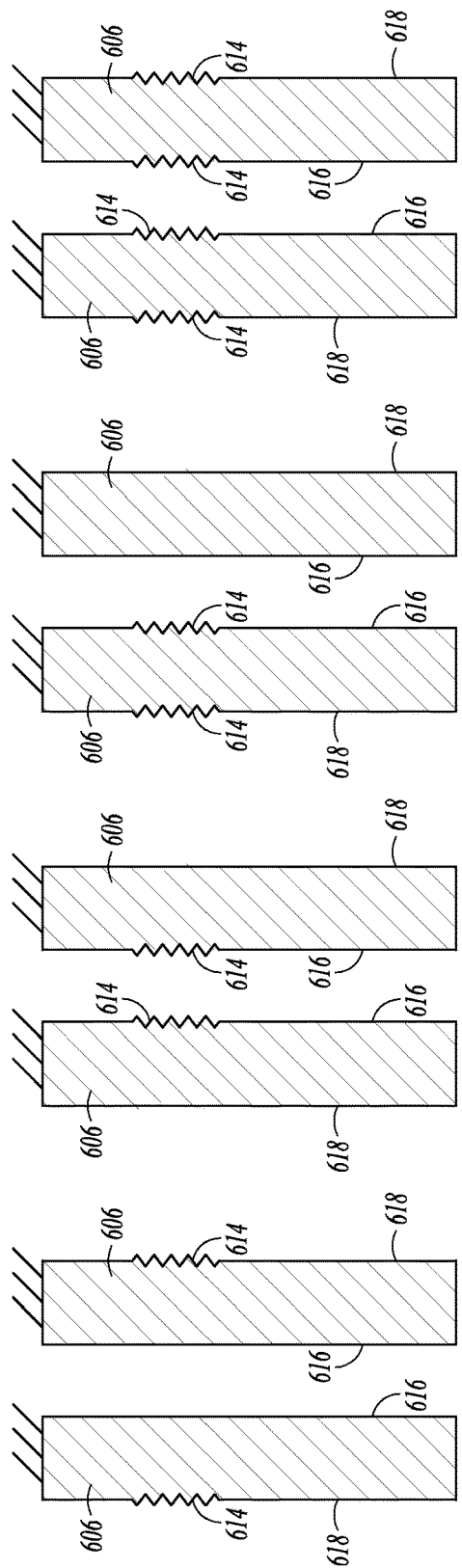

CANNULA WITH SENSORS TO MEASURE PATIENT BODYWALL FORCES

CLAIM OF PRIORITY

This application is a U.S. National Stage Filing under 35 U.S.C. 371 from International Application No. PCT/US2015/042262, filed on Jul. 27, 2015, and published as WO 2016/018815 A1 on Feb. 4, 2016, which claims the benefit of priority under 35 U.S.C. § 119(e) to U.S. Provisional Patent Application No. 62/030,468, filed on Jul. 29, 2014, each of which is hereby incorporated by reference herein in its entirety.

FIELD

The invention relates in general to minimally invasive surgical systems, and more particularly, to a cannulas used during minimum invasive surgery.

BACKGROUND

Endoscopy may be the most common form of minimally invasive surgery. Perhaps the most common form of endoscopy is laparoscopy, which is minimally invasive inspection and surgery inside the abdominal cavity. In a typical laparoscopic surgery, a patient's abdomen is insufflated with gas, and cannula sleeves are passed through small (approximately ½ inch) incisions to provide entry ports for laparoscopic surgical instruments.

As explained in U.S. Pat. No. 6,989,003, entitled, "Obturator and Cannula for a Trocar Adapted for Ease of Insertion and Removal", a trocar-cannula, commonly referred to as, a trocar, is a surgical device used to obtain access to a body cavity to perform various surgical procedures, such as, laparoscopic surgery or arthroscopic surgery. Typically, a trocar is an elongated, pointed surgical instrument that includes a pointed rod-like device, referred to in the art as an "obturator" that is fitted into a tube-like device that is referred to in the art as a "cannula". The pointed, sometimes sharply pointed, end of the obturator projects out the end of the cannula and is used to penetrate the outer tissue of the cavity. After the tissue is penetrated and the body cavity, for example, is accessed by the trocar, the obturator is withdrawn from the cavity and the cannula is left in place in the cavity to provide a channel for accessing the cavity. The body cavity can then be accessed by further surgical instruments via the cannula to perform various surgical procedures.

The laparoscopic surgical instruments generally include a laparoscope for viewing the surgical field, and working tools defining end effectors. Typical surgical end effectors include clamps, graspers, scissors, staplers, or needle holders, for example. The working tools are similar to those used in conventional (open) surgery, except that the working end or end effector of each tool is separated from its handle by, e.g., an approximately 12-inch long, extension tube.

To perform surgical procedures, the surgeon passes these working tools or instruments through cannula sleeves to a required internal surgical site and manipulates them from outside the abdomen by sliding them in and out through the cannula sleeves, rotating them in the cannula sleeves, levering (i.e., pivoting) the instruments against the abdominal wall and actuating end effectors on the distal ends of the instruments from outside the abdomen. The instruments pivot around centers defined by the incisions which extend through muscles of the abdominal wall. The surgeon monitors the procedure by means of a television monitor which displays an image of the surgical site via a laparoscopic camera. A laparoscopic camera is also introduced through the abdominal wall and into the surgical site. Similar endoscopic techniques are employed in, e.g., arthroscopy, retroperitoneoscopy, pelviscopy, nephroscopy, cystoscopy, cisternoscopy, sinoscopy, hysteroscopy, urethroscopy and the like.

U.S. Pat. No. 7,155,315, entitled, "Camera Referenced Control in a Minimally Invasive Surgical Apparatus", describes a minimally invasive telesurgical system for use in surgery to increase a surgeon's dexterity as well as to allow a surgeon to operate on a patient from a remote location. Telesurgery is a general term for surgical systems where the surgeon uses some form of remote control, e.g., a servomechanism, or the like, to manipulate surgical instrument movements rather than directly holding and moving the instruments by hand. In such a telesurgery system, the surgeon is provided with an image of the surgical site at the remote location. While viewing typically a three-dimensional image of the surgical site on a suitable viewer or display, the surgeon performs the surgical procedures on the patient by manipulating master control devices, at the remote location, which control the motion of servomechanically operated instruments.

The servomechanism used for telesurgery will often accept input from two master controllers (one for each of the surgeon's hands), and may include two robotic arms. Operative communication between each master control and an associated arm and instrument assembly is achieved through a control system. The control system includes at least one processor which relays input commands from a master controller to an associated arm and instrument assembly and from the arm and instrument assembly to the associated master controller in the case of, e.g., force feedback.

FIG. 1 is an illustrative drawing showing a known cannula 102 that acts as a conduit for receiving one or more instruments 104 extending through a patient's bodywall 106. The cannula includes a proximal end portion 108 disposed outside the body cavity and a distal end portion 110 that extends within the body cavity. An instrument 104 typically includes an elongated shaft portion 104-1 having an end effector portion 104-2 coupled to a distal working-end thereof. In operation, longitudinal axes of the instrument 104 and the cannula 102 are aligned when the instrument is inserted in the cannula. In some telesurgical systems, a wrist-like mechanism 104-3 is located at the distal end of the instrument between the shaft 104-1 and the end-effector 104-2 to allow rotational movement of the end effector within the body cavity.

Typically, during minimally invasive surgery, a surgeon manipulates the instrument 104 to perform a surgical procedure from a distance, which diminishes the surgeon's ability to use physical touch as a source of feedback during surgery. The surgeon may manipulate an end effector 104-2 disposed at the end of an elongated instrument shaft 104-1 that extends through a cannula 102, for example. As a consequence, a surgeon's may lose the ability to sense the amount of force exerted upon internal body tissue during the procedure. U. S. Patent Application Pub. No. 2011/0178477, entitled, Trocar Device for Passing a Surgical Tool, and N. Zemiti et al., A Force Controlled Laparoscopic Surgical Robot without Distal Force Sensing, Experimental Robotics IX, STAR 21, pages 153-163, Springer-Verlag Berlin Heidelberg 2006, disclose trocar that include sensors used to estimate the force exerted by an elongated instrument upon internal body tissue contacted by a surgical instrument during minimally invasive surgery.

SUMMARY

A cannula includes a head portion that defines a proximal opening sized to receive one or more surgical instruments. An elongated inner tube rigidly fastened to the head portion defines an elongated conduit between the proximal opening and a distal opening. One or more surgical instruments can be inserted in through the proximal opening and extend through the conduit to the distal opening. An elongated overtube is rigidly fastened to the head portion and is coaxially aligned with the inner tube and extends about a portion of the inner tube. An inner wall of the overtube is apart from an outer wall of the inner tube. Sensors are disposed on the overtube to provide an indication of forces applied to the outer wall of the overtube in a direction generally transverse to the longitudinal dimension of the overtube.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIGS. 6C1-6C4 are illustrative drawings showing longitudinal cross-sectional views of a portion of the overtube with four alternative sensor placement configurations in accordance with some embodiments.

DESCRIPTION OF EMBODIMENTS

Figure 1:
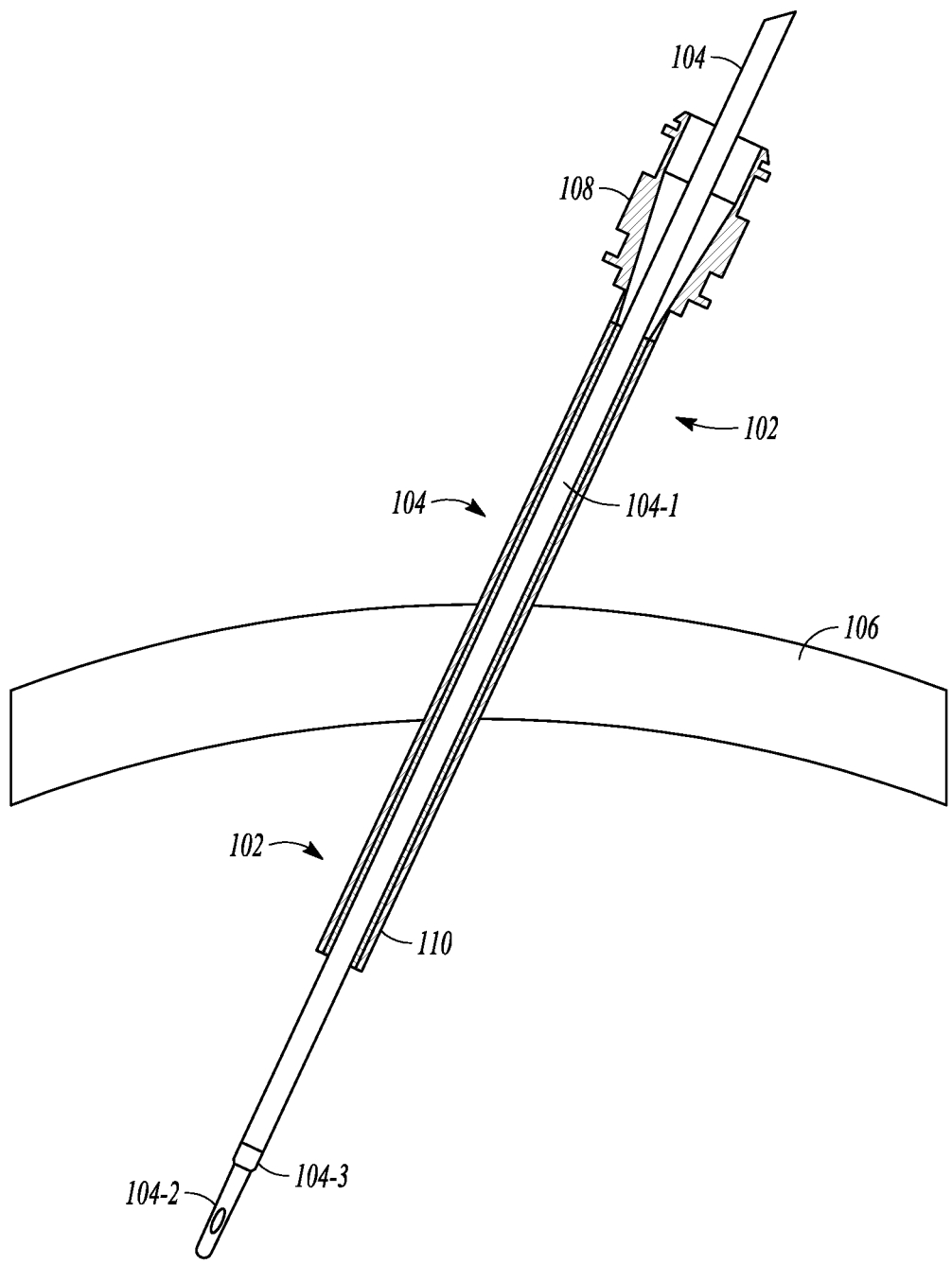
FIG. 1 is an illustrative side elevation cross-sectional view drawing showing a known cannula that acts as a conduit for one or more instruments extending through a patient's bodywall.

The following description is presented to enable any person skilled in the art to create and use a cannula with sensors isolated from forces resulting from instrument-cannula collisions. Various modifications to the embodiments will be readily apparent to those skilled in the art, and the generic principles defined herein may be applied to other embodiments and applications without departing from the spirit and scope of the inventive subject matter. Moreover, in the following description, numerous details are set forth for the purpose of explanation. However, one of ordinary skill in the art will realize that the inventive subject matter might be practiced without the use of these specific details. Identical reference numerals may be used to represent different views of the same item in different drawings. Thus, the inventive subject matter is not intended to be limited to the embodiments shown, but is to be accorded the widest scope consistent with the principles and features disclosed herein.

Figure 2:
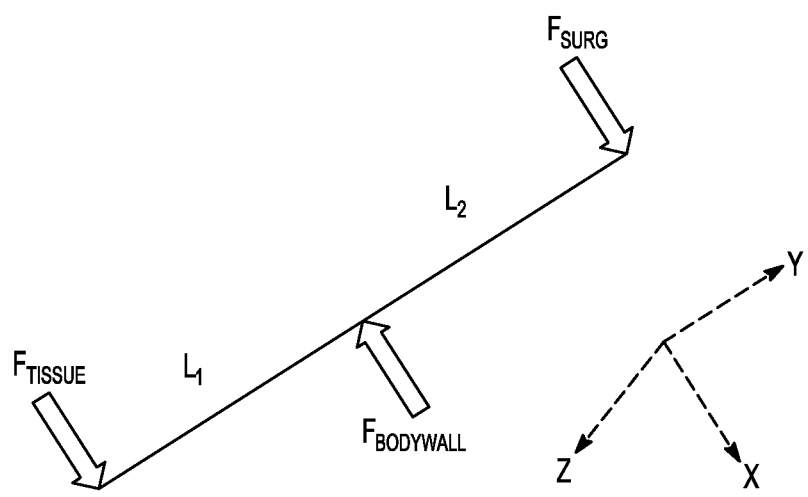
FIG. 2 is an illustrative drawing representing certain forces exerted upon an instrument inserted within a cannula and resultant force upon a patient's bodywall.

FIG. 2 is an illustrative drawing representing certain forces exerted upon an instrument inserted within a cannula and resultant force upon a patient's bodywall. Both during laparoscopic surgery and telesurgery, insertion and movement of the cannula and instruments inserted within the cannula results in forces exerted upon a patient's abdominal bodywall. The cannula and an instrument inserted within the cannula have longitudinal axes, e.g., that extend generally parallel to a y-axis as shown. A surgeon, during laparoscopic surgery or telesurgery, may impart to a proximal end of the instrument that is disposed outside the patient's body, a lateral force having a force component generally perpendicular to the longitudinal axes of the cannula and the instrument. The surgeon force upon the instrument is imparted to the cannula. In reaction, internal body tissue that is contacted by a distal end of the instrument, inside the body cavity, may exert to a distal end of the instrument that is disposed inside the patient's body, a lateral force having a force component directed generally perpendicular to the longitudinal axes of the cannula and the instrument. The internal body tissue force upon the instrument is imparted to the cannula. The bodywall, which is disposed between a site of the surgeon imparted force and a site of the tissue imparted force, exerts a lateral direction reactive force, in response to a combination of the surgeon's force and the tissue's force having a force component directed generally perpendicular to the vertical axis of the cannula. More specifically, forces created in response to manipulation of instruments inserted within a cannula create a lever action in which a patient's bodywall is disposed at or near the fulcrum. These forces associated with the lever action exert stresses upon the bodywall tissue that can result in tissue trauma.

Figure 3A:
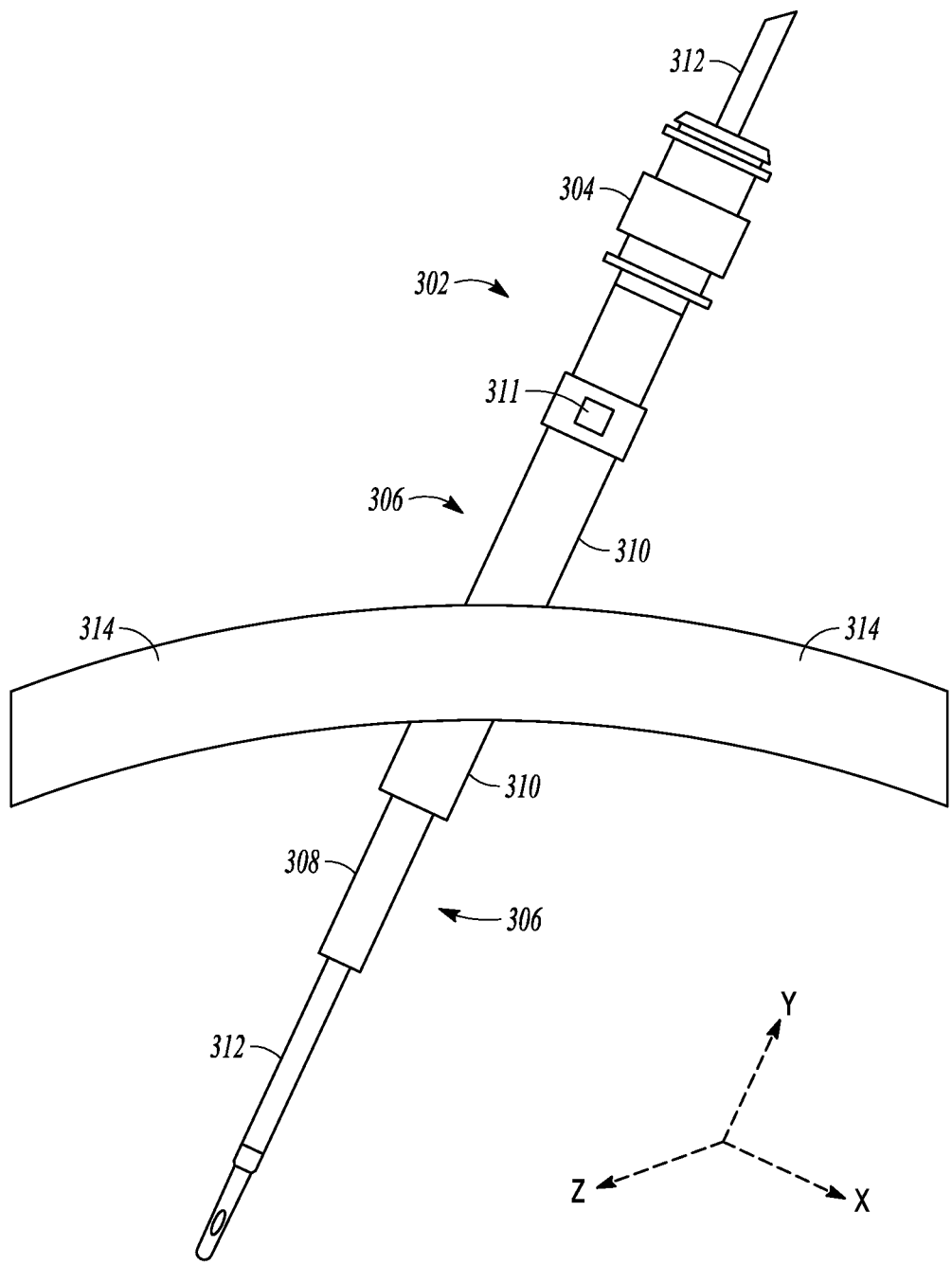
FIG. 3A is an illustrative side elevation drawing of a first cannula in accordance with some embodiments.
Figure 3B:
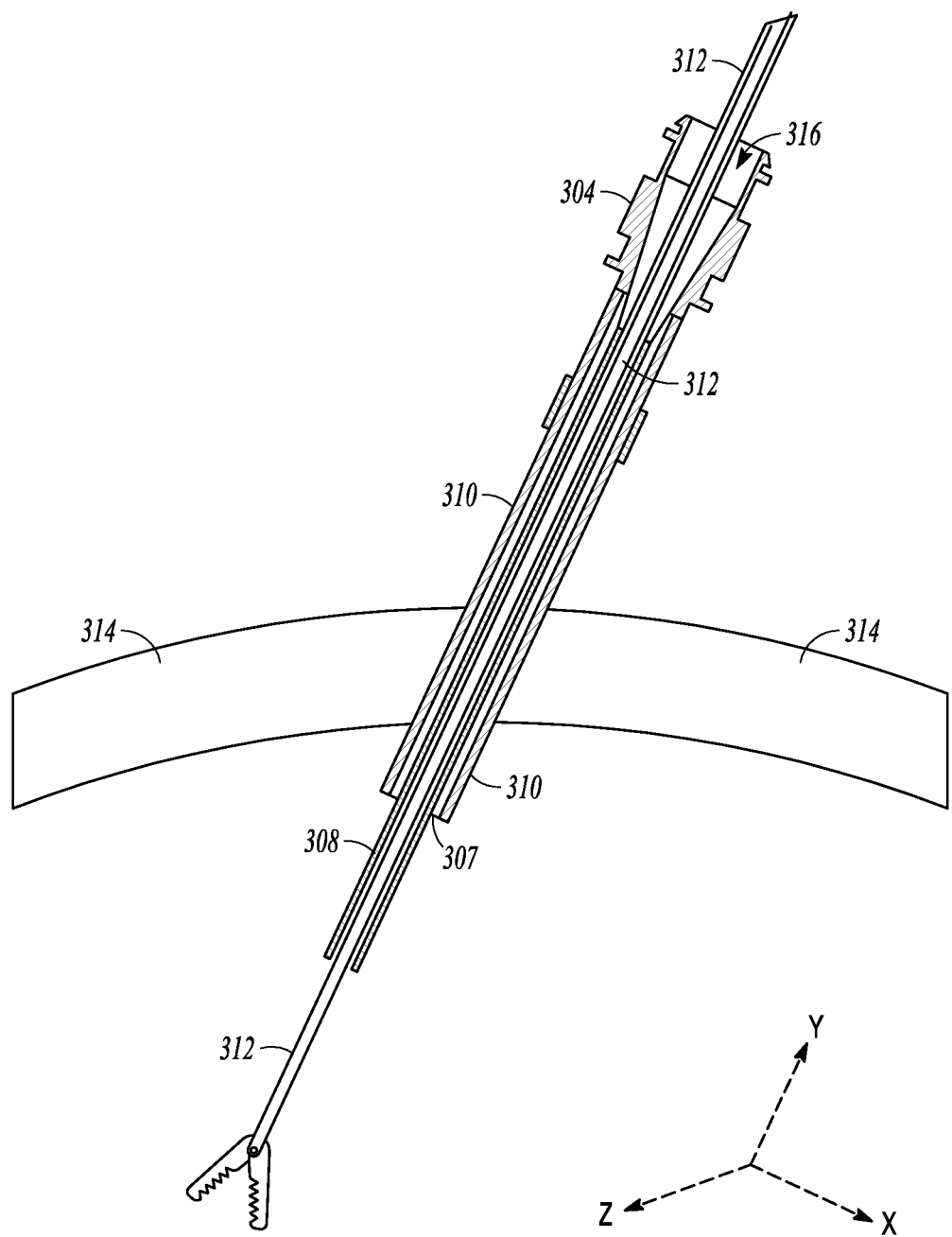
FIG. 3B is a cross-sectional view of the first cannula of FIG. 3A in accordance with some embodiments.

FIG. 3A is an illustrative side elevation drawing of a first cannula 302 in accordance with some embodiments. FIG. 3B is a cross-sectional view of the first cannula 302 of FIG. 3A in accordance with some embodiments. The first cannula 302 includes a head portion 304 and an elongated portion 306 that includes a coaxial elongated inner tube 308 and elongated overtube 310. The elongated portion 306, which includes the elongated inner tube 308 and elongated overtube 310 are generally cylindrical in contour. The elongated portion 306 depends from the head portion 304. More particularly, the inner tube 308 and the overtube 310 are rigidly fastened (i.e. welded or otherwise mechanically connected) to the head portion 304. In some embodiments, the inner tube 308 and the overtube 310 are formed integrally with the head portion.

The inner tube 308 includes inner walls that define an elongated inner conduit sized to receive one or more surgical instruments 312 (only one shown). The overtube 310 surrounds at least a portion of the inner tube 308, and extends distally enough to come into contact with the bodywall such that all the loads from the bodywall are imparted on the overtube and not the inner tube. The inner tube 308 is longer than the overtube 310, and therefore, extends distally past the distal end of the overtube 310. The inner tube 308 extending beyond the distal end of the overtube ensures that the instrument does not come into direct contact with the overtube during normal operation. The first cannula is shown with the elongated portion 306 extending through a patient's bodywall 314. The inner tube 308 has a lateral dimension that is sized to receive one or more surgical instruments and defines a distal opening at a distal end so as to provide surgical access within the patient's body. As more fully clearly represented in FIGS. 6A-6B, which are explained below, the overtube 310 is coaxially aligned with the inner tube 308 and is laterally spaced apart therefrom so as to not contact the inner tube 310 during normal operation. More particularly, as shown more clearly in FIGS. 6A-6B, the inner tube outer diameter is sufficiently smaller than the overtube inner diameter so that the inner tube and the overtube do not come into contact during normal operation. Sensor devices 311 disposed in contact with the overtube 310 wall are configured to provide an indication of forces imparted to the overtube 310 by the bodywall 314.

During a typical surgical procedure, the head portion 304 of the first cannula 302 is disposed outside of the patient's body cavity, and at least a portion of the elongated portion 306, which includes a portion of the inner tube 308 and a portion of the overtube 310, extends through the bodywall 314 to an interior of the patient's body cavity. The elongated portion 306 has a longitudinal axis, e.g., generally parallel to a y-axis as shown. One or more surgical instruments can be inserted through the head portion 304 and extend generally parallel to the center axis through an instrument-receiving conduit defined by the inner tube 308 so as to project out from the open distal end of the inner tube to the interior of a patient's body.

In some embodiments, the head portion 304 and the inner tube 308 comprise an integral structure that defines the instrument-receiving conduit in which the one or more instruments may be inserted. The head portion 304 defines a proximal opening 316 to the conduit. The proximal opening is enlarged so as to provide ease in insertion and removal of instruments, and conduit walls within the head portion are inclined so as to provide guide surfaces to guide instruments to the narrower diameter elongated portion of the conduit defined by the inner tube. In some embodiments, the head portion 304 also includes a gas conduit (not shown) to introduce one or more gases through the inner tube for insufflating the body cavity during a surgical procedure. In some embodiments, the head portion 304 also includes a seal (not shown) for preventing gas from escaping the body cavity during insufflation in a surgical procedure. In some embodiments adapted for use during laparoscopic surgery, the head portion 304 is sized and shaped to be held by a surgeon, for example, during insertion of a trocar (not shown) or withdrawal of an obturator (not shown), which form no part of the present invention.

The overtube 310 has stiffness such that it can deflect at one or more locations along its longitudinal axis in response to forces imparted generally transverse to its longitudinal axis by a patient's bodywall 314, e.g., including forces imparted generally in an x-axis or a z-axis direction, during a typical surgical procedure. Moreover, the overtube 310 stiffness and its lateral spacing from the inner tube 308 are such that an inner wall of the overtube and an outer wall of the inner tube do not physically contact each other when the overtube deflects relative to its longitudinal center axis in response to forces imparted to a patient's bodywall 314 during a typical surgical procedure. In some embodiments, spacing between the overtube and the inner tube comprises a gap 307, which is represented more clearly in FIGS. 6A-6B as gap 607, which is narrow enough to not add significantly to overall diameter of the elongated portion 306 of the cannula 302 so as to not significantly increase the size of a surgical incision required to insert the elongated portion 306 into a patient's body.

During normal operation, the gap region 307 (described more fully below and illustrated with reference to FIGS. 6A-6B) defined between the inner tube and the overtube isolates the overtube 310 from deflections that may be imparted to the inner tube 308 due to instrument contact with the inner tube in the course of a surgical procedure, for example. Such instrument contact may involve an instrument banging against an inner wall of the inner tube due to a surgeon's or a teleoperated robot's manipulation of instruments during a surgical procedure. The sensor devices (described more fully below) in contact with the overtube 310, therefore, are isolated from the effects of deflection forces imparted due to collisions between the instrument and the inner tube 308. Thus, a cannula in accordance with some embodiments can disambiguate forces imparted by instrument collisions with an inner wall of the inner tube from bodywall loads imparted to the overtube.

Figure 4:
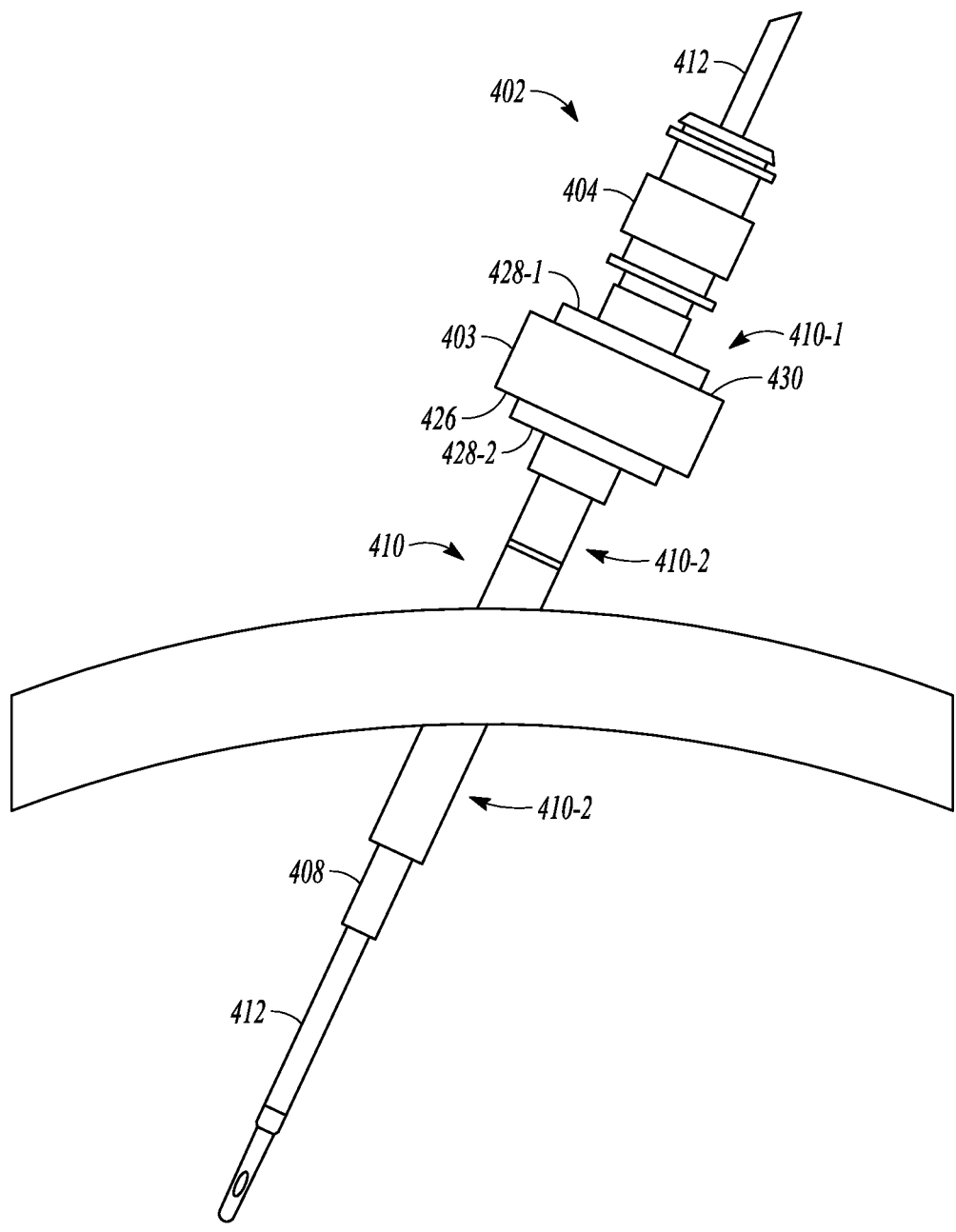
FIG. 4 is an illustrative side elevation drawing of a second cannula in accordance with some embodiments.

FIG. 4 is an illustrative side elevation drawing of a second cannula 402 in accordance with some embodiments. Features of the second cannula that are substantially identical to those of the first cannula 302 are identified by the same reference numerals used to identify the corresponding features in FIGS. 3A-3B and are not further described. The second cannula 402 includes a six degree-of-freedom (6-dof) sensor device 403. In some embodiments, the 6-dof sensor 403 includes a Stewart platform based force/torque sensor. The second cannula 402 includes a head portion 404 and coaxially aligned elongated inner tube 408 and elongated overtube 410. The inner tube 408 is sized to receive one or more surgical instruments 412 (only one shown). The overtube 410 of the second cannula 402 includes a first overtube portion 410-1 and a second overtube portion 410-2, and the 6-dof sensor 403 is disposed between the first and second overtube portions.

Figure 5:
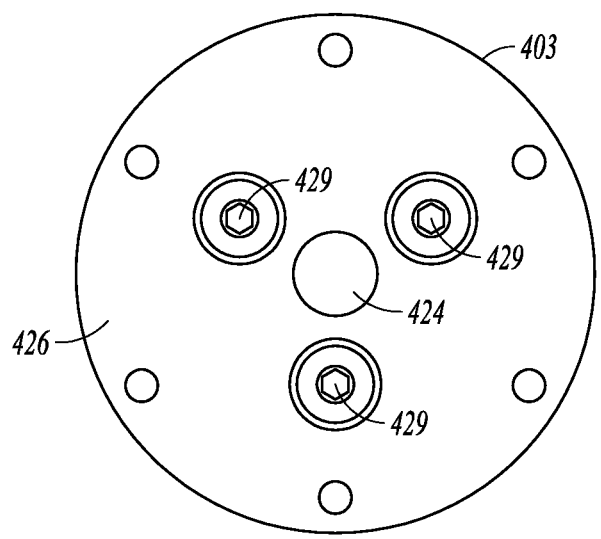
FIG. 5 is a perspective view of a six degree-of-freedom sensor in accordance with some embodiments.

FIG. 5 is a perspective view of a six degree-of-freedom sensor 403 in accordance with some embodiments. The 6-dof force/sensor has an annular shape that defines a central opening 424 through which instruments (not shown) and the inner tube 408 can extend. In some embodiments, the 6-dof sensor includes silicon strain gages to sense forces. Referring again to FIG. 4, first overtube portion 410-1 rigidly depends from a head portion 404 of the second cannula 402. The first overtube portion 410-1 includes a distal end that defines a first annular flange 428-1 sized to operatively contact a proximal surface region 430 of the 6-dof sensor 403. The second overtube portion 410-2 includes a proximal end that defines a second annular flange 428-2 sized to operatively contact a distal surface region 426 of the 6-dof sensor 403. Attachment fasteners (e.g., screws) 429 are visible also.

Figure 6A:
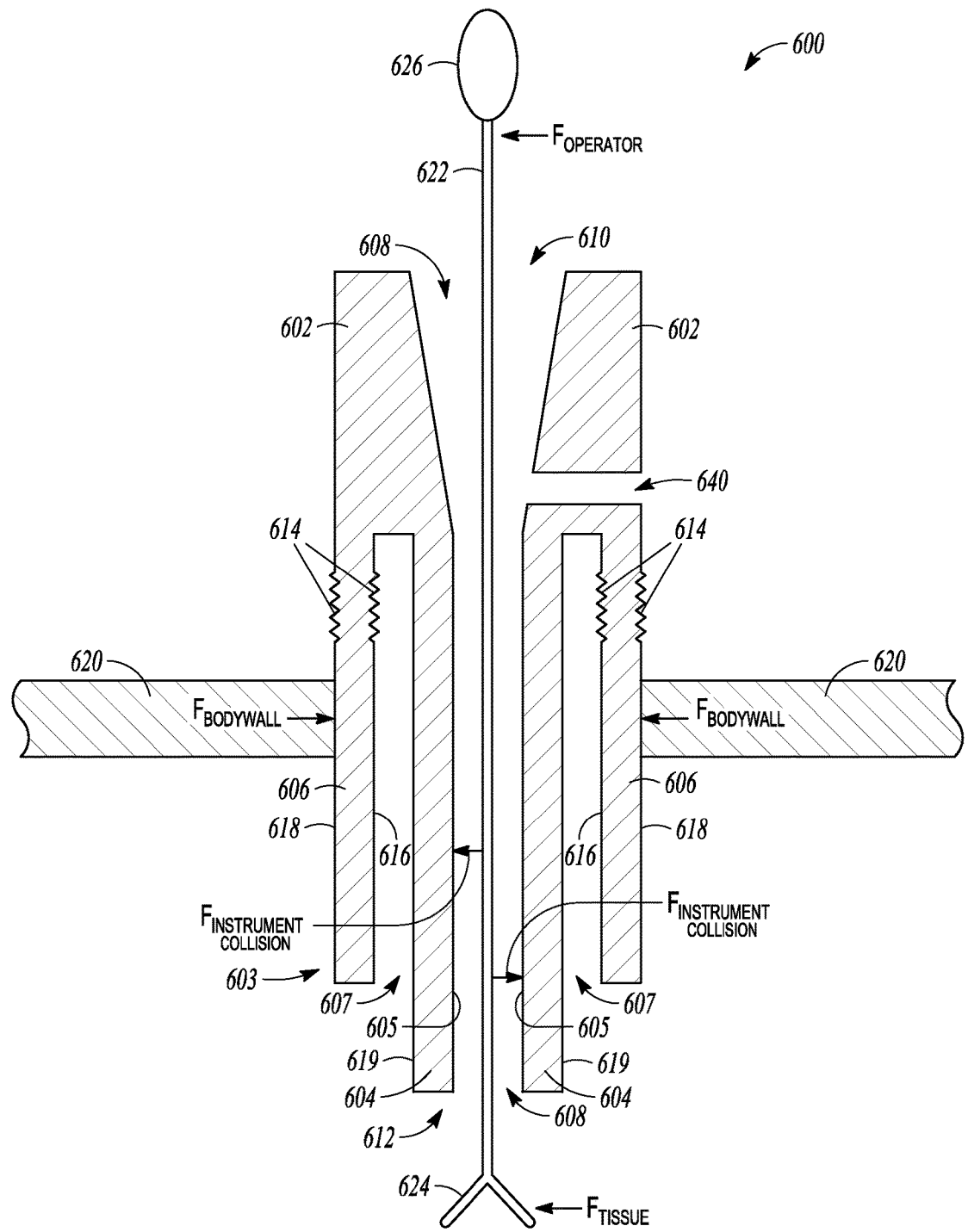
FIG. 6A is an illustrative cross-sectional drawing of the first cannula showing an instrument disposed to collide with an inner tube in accordance with some embodiments.

FIG. 6A is an illustrative cross-sectional drawing of the first cannula 600 representing an example collision between an instrument 622 and the inner tube 604 in accordance with some embodiments. The first cannula 600 includes the head portion 602 and the elongated portion 603. The head portion 602 defines an insufflation conduit 640 through which an insufflating gas can be introduced inside the inner tube 604 and inside the patient's body cavity via the inner tube during a surgical procedure. The elongated portion 603 includes the coaxial inner tube 604 and overtube 606, which depends from the head portion 602. The inner tube includes an inner wall 605 that defines the instrument-receiving conduit and an outer wall 619. The gap 607 is defined by an outer wall 619 of the inner tube and an inner wall 616 of the overtube. Together, the head portion 602 and the inner wall 605 of the inner tube 604 define the instrument-receiving conduit 608. The head portion 602 defines the proximal opening 610 to the conduit 608. A distal end of the inner tube 604 defines a distal opening 612 to the conduit 608 adjacent to a patient's body cavity. Strain sensors 614 are disposed to contact an inner wall 616 of the overtube 604 and/or an outer wall 618 of the overtube 604 and are configured to measure strain imparted to the overtube.

Referring to the illustrative drawings of FIGS. 6C1-6C4, there are shown longitudinal cross-sectional views of a portion of the overtube 606 with four alternative sensor placement configurations in accordance with some embodiments. FIG. 6C1 shows an illustrative first sensor placement on outer wall 618 of the overtube 606. On one side of the outer wall 618, there is a sensor 614 and 180 degrees apart on the opposite outer wall 618 from that sensor 614 there is the complementary sensor 614. FIG. 6C2 shows an illustrative second sensor placement on inner wall 616 of the overtube 606. On one side of the inner wall 616, there is a sensor 614 and on an opposed facing portion of the inner wall 616 there is the complementary sensor 614. FIG. 6C3 shows an illustrative third sensor placement on both inner wall 616 and outer wall of the overtube 606. On the inner wall 616, there is a sensor 614 and on a portion of the outer wall 618 directly opposite that sensor 614 there is a complementary sensor 614. FIG. 6C4 shows an illustrative fourth sensor placement with redundant sensor placements like that of FIG. 6C3.

Referring again to FIG. 6A, during performance of a surgical procedure, the first cannula 600 extends through a patient's bodywall 620, and an instrument 622 extends within the conduit 608 to reach inside the patient's body cavity. The instrument 622 may include an end-effector 624 for use in performing a surgical procedure. An operator 626, such as a surgeon or a teleoperation surgical system manipulates the instrument 622 while it extends within the conduit 608 and into a patient's body.

During the procedure, a force $F_{Operator}$ imposed by the operator 626 upon the instrument 622 and/or a force $F_{Tissue}$ imposed by patient tissue upon the instrument 622 may cause the instrument to collide with the inner wall 605 of the inner tube 604, which imparts a force $F_{Instrument}$ upon the inner wall 605 of the inner tube 604. However, the instrument collision force is not imparted to the overtube 606 since it is isolated from the inner tube 604 by the gap 607. Thus the sensors 614 configured to sense strain in the overtube 606 do not detect deflections from force $F_{Instrument}$ imparted due to collisions between the instrument 622 and the inner tube 604.

It will be appreciated that the force $F_{Instrument}$ upon the inner wall 605 of the inner tube 604 imparts a load through the overtube 606 to the patient's bodywall. However, the gap 607 between the inner tube 604 and the overtube 606 isolates the overtube 606 from incurring deflections due to collisions between the inner tube 604 and the instrument 622. Thus, deflections imparted to the overtube 606 result from patient bodywall forces, which may be responsive to a force $F_{Instrument}$ upon the inner wall 605 of the inner tube 604, but such deflections are not imparted due to the collisions between the instrument 622 and the overtube 606, since there are no such collisions.

The overtube 606 has a stiffness such that it can deflect relative to its longitudinal axis in response to lateral forces imparted by the patient's bodywall 620, in a direction generally perpendicular to its longitudinal axis, e.g. in an x-axis or z-axis direction, but having an component force in the y-axis when the angle between the cannula and bodywall, e.g., $\Theta$, is not 90 degrees. Additionally the overtube 606 has a compressive strength such that it can compress or stretch along it's longitudinal axis in response to non-lateral bodywall forces, e.g. in the y-axis direction.

More specifically, in some embodiments the overtube stiffness has a predictable and linear strain response to stress, i.e. a known young's modulus. More specifically, in some embodiments, the stiffness of the overtube is great enough for the tube to deflect and not permanently deform under typical body wall loads of approximately 0-30 Newtons. Even more specifically, in some embodiments, the stiffness of the overtube is great enough for the tube to deflect and not permanently deform under loads of approximately 0-50 Newtons. In some embodiments, a stainless steel overtube with a wall thickness of approximately 0.005-0.050, with a preferred of approximately wall thickness range of approximately 0.012-0.030, and an outside diameter of approximately 0.25-1 inches, with a preferred range of approximately 0.4-0.6 inches, has an acceptable stiffness to deflect but not permanently deform under normal loads from the bodywall. Preferably, in some embodiments, Spacing between the overtube and the inner tube should be great enough such that the inner diameter (ID) of the overtube does not touch the outer diameter (OD) of the inner tube when the overtube deflects, but small enough such that the outer diameter of the overtube represents typical cannula diameters in minimally invasive surgery. In some embodiments, the spacing, 607 of FIG. 6A, between the overtube ID and inner tube OD is approximately 0.007-0.1 inches, with a preferred range of approximately 0.015-0.035 inches.

Figure 6B:
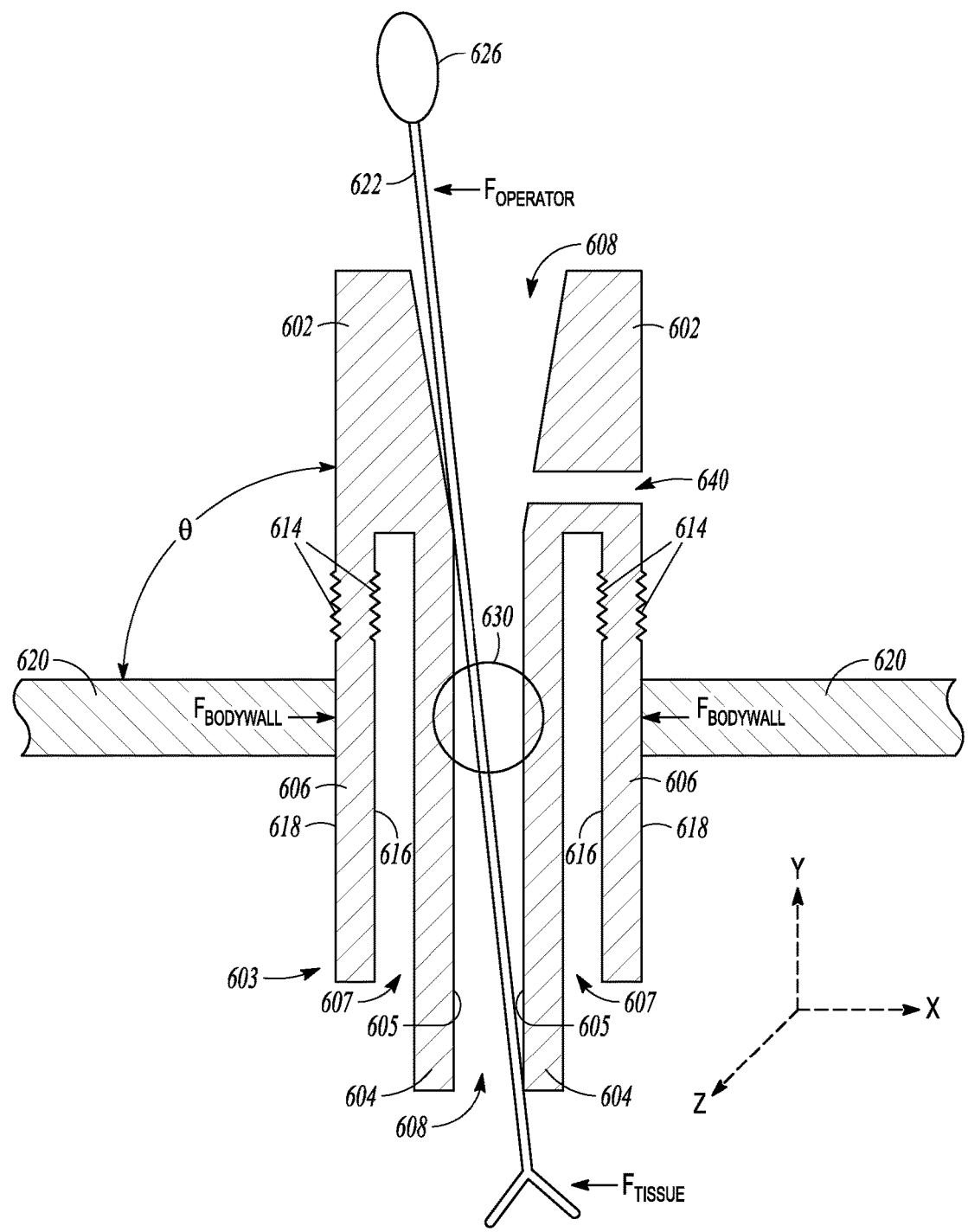
FIG. 6B is an illustrative cross-sectional drawing of the first cannula showing an instrument disposed to impart a lever force to an inner tube in accordance with some embodiments.

FIG. 6B is an illustrative cross-sectional drawing of the first cannula 600 showing an instrument 622 disposed to impart a lever force to the inner tube 604 in accordance with some embodiments. It will be appreciated that FIG. 6A and FIG. 6B are identical except for the disposition of the instrument within the inner tube and the forces imparted. Assume that an operator imparts a force $F_{Operator}$ and the tissue imparts a force $F_{Tissue}$ that cause the instrument 622 to push to the left in FIG. 6B against an inner wall 605 of the inner tube 604 adjacent a proximal end of the inner tube 604 and that cause the instrument 622 to push to the right in FIG. 6B against the inner wall 605 of the inner tube 604 adjacent a distal end of the inner tube 604. Under these conditions, for example, the first cannula 600 acts as a lever having a fulcrum at a location generally indicated by dashed lines 630, at about the location of the bodywall 620.

Under these conditions, a bodywall force $F_{Bodywall}$ is imparted to the patient's bodywall 620. The bodywall force can be a torque or a force, for example, in which a distal end of the overtube 606 imparts a force in a direction generally to the right in the drawing and a proximal end of the overtube 606 imparts a force in a direction generally to the left in the drawing, for example. The torque force to the overtube 606 about an x-axis and/or the z-axis, for example, centered at about the location of the bodywall 620. In accordance with some embodiments, the bodywall force $F_{Bodywall}$ is imparted to the overtube 606, which may deflect in response to the bodywall force. The sensors 614 can detect strain in the overtube that results from the force or torque and can provide a measure of the strain.

The sensor devices 614 are disposed in physical contact with the overtube 606 to measure deflection of the overtube 606. Sensor devices can be disposed in contact with an external wall 618 of the overtube, in contact with an interior wall 616 of the overtube or in contact with both. In some embodiments, the sensor devices 614 are configured to act as strain gauges. Strain is a measure of the amount of deformation of a body due to an applied force. More specifically, strain can be defined as the fractional change of length.

Figure 7:
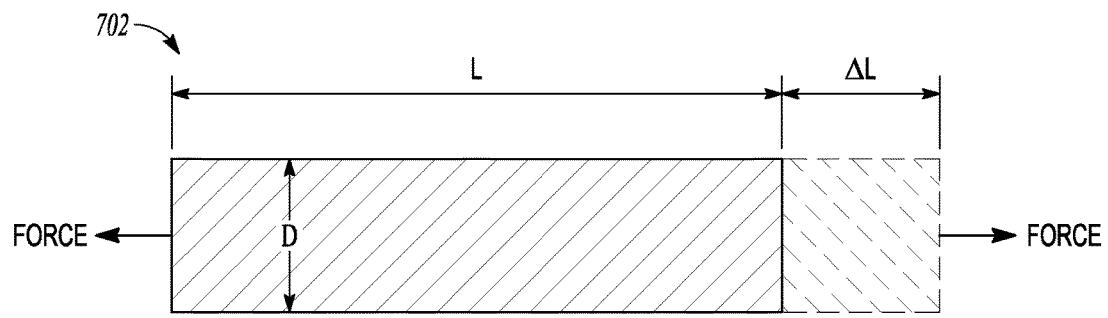
FIG. 7 is an illustrative drawing representing an object that is subjected to axial force that changes its length dimension.

FIG. 7 is an illustrative drawing representing an object 702 that is subjected to axial force that changes its length dimension. The length of the object in the absence of the forces is L. The change in the object's length in response to the forces is ΔL.

Strain can be defined as: $\varepsilon = \Delta L/L$.

Figure 8:
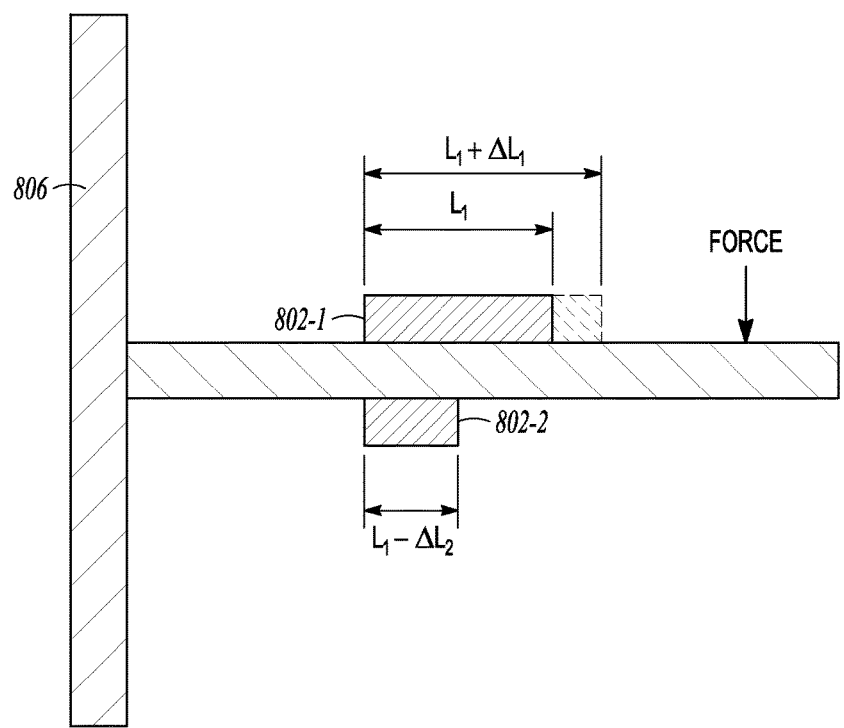
FIG. 8 is an illustrative drawings showing example of strain gauges mounted on opposite sides of a longitudinal structure subjected to a force transverse to a longitudinal axis of the structure.

FIG. 8 is an illustrative drawings showing example of first and second strain gauges 802-1, 802-2 mounted on opposite sides of a longitudinal structure 804 that depends horizontally from a fixture 806 and that is subjected to a force transverse to a longitudinal axis (L) of the structure 804. An example generally downward uniaxial force imparted transverse to a longitudinal axis of the structure places the first strain gauge 802-1 having an at rest length $L_1$ mounted on a side of the structure to which the force is imposed in tension, resulting in an increase in the length dimension of the first strain gauge 802-1 to $L_1 + \Delta L_1$. Conversely, the downward uniaxial force imparted transverse to the longitudinal axis of the structure 804 places the second strain gauge 802-2 having an at rest length $L_1$ mounted on a side of the structure 804 opposite to that to which the force is imposed in compression, resulting in a decrease in the length dimension of the second strain gauge 802-2 to $L1 - \Delta L_2$. In accordance with some embodiments, strain gauges are mounted to the inner wall 616 and the outer wall 618 of the overtube 606 and may be spaced around the overtube in a variety of configurations in order to measure the applied forces in multiple directions.

As explained above with reference to FIG. 6B, moments from the bodywall can create complex tube deflection that includes tension and compression simultaneously along various points in length of the loaded member. In some embodiments, such moments can be calculated when a staggered configuration of strain gauges is used because the strain gauges are experiencing both tension and compression at known points along inner and outer walls of the surface of the overtube.

Figure 9:
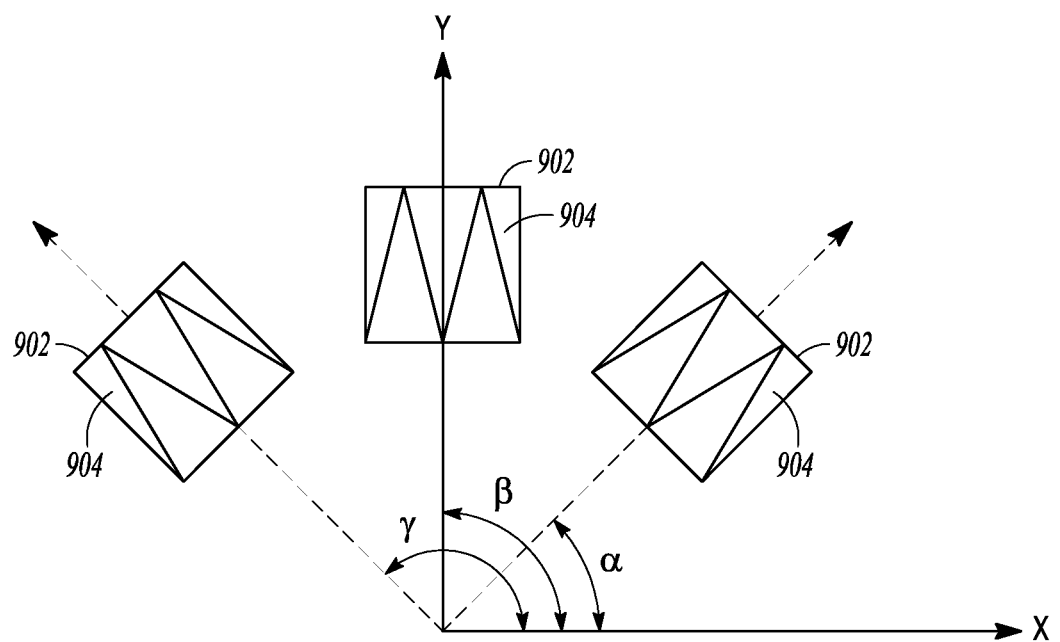
FIG. 9 is an illustrative drawing of showing strain gauges arranged in a rosette-like configuration in accordance with some embodiments.

FIG. 9 is an illustrative drawing of showing strain gauges 902 arranged in a rosette-like configuration in accordance with some embodiments. Strain gauges are well known to persons of ordinary skill in the art. In some embodiments, a strain gauge may comprise a grid pattern 904 that includes a very fine metallic wire, foil, fiber, etc. arranged in a grid pattern. The grid 904 is bonded to a thin backing (not shown), commonly referred to as a carrier which is directly attached to an item for which strain is to be measured. Strain that is experienced by such item is transferred directly to the strain gauge, which responds with a known, e.g., linear, change in electrical resistance. In a rosette-like configuration, multiple strain gauges are positioned at known angles (e.g., α, β, γ) to one another in a rosette-like layout to convert longitudinal strain into three independent components of plane strain. In accordance with some embodiments, groupings of sensors arranged in a rosette structure can be staggered along the inner wall 616 and outer wall 618 of the overtube 606 to measure moments about the x-axis and z-axis.

Figure 10:
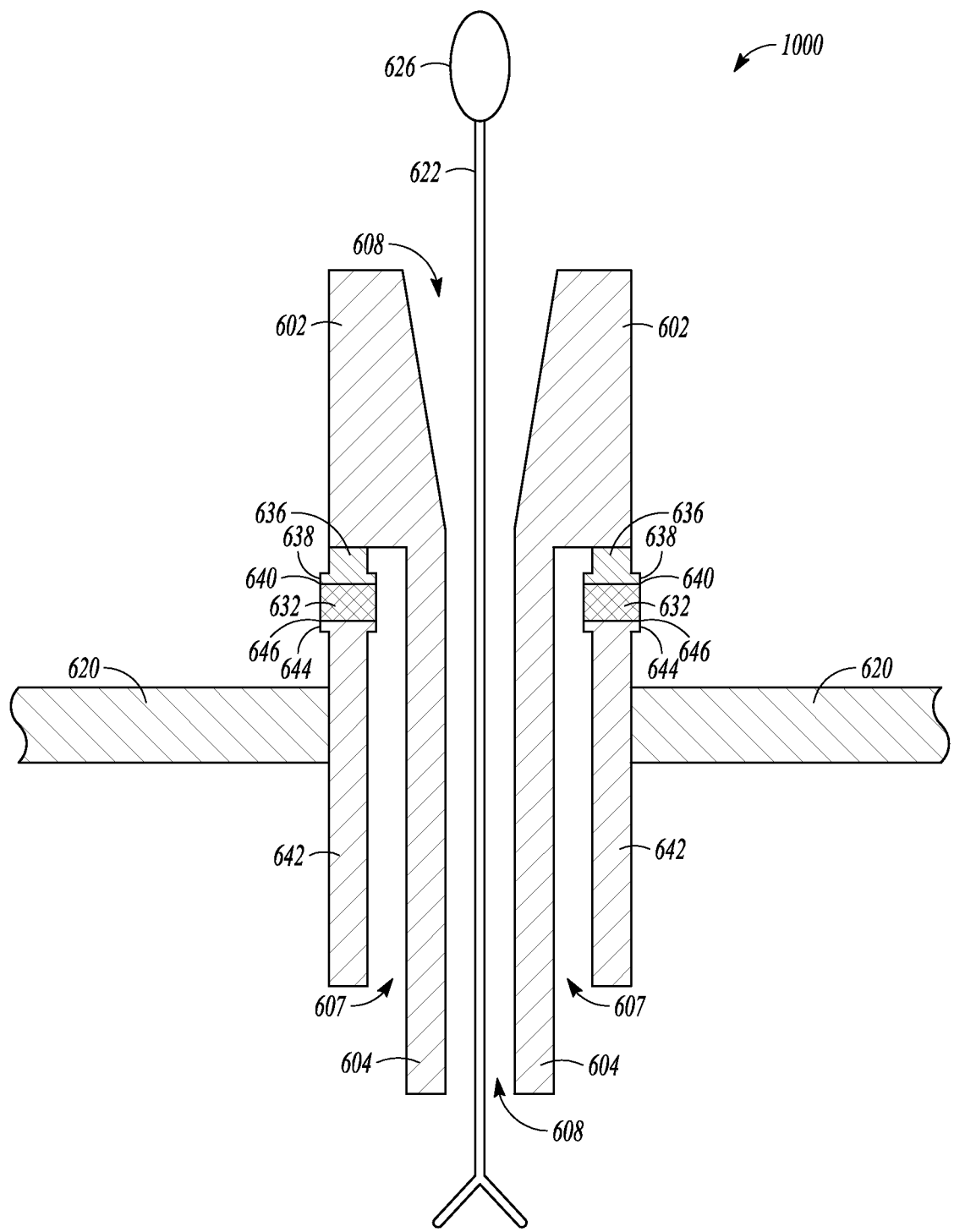
FIG. 10 is an illustrative cross-sectional drawing of the second cannula in accordance with some embodiments.

FIG. 10 is an illustrative cross-sectional drawing of the second cannula 1000 in accordance with some embodiments. The second cannula 1000 includes an annular 6-dof sensor 632. The overtube 606 includes the first overtube portion 636 that includes the first annular flange 638 sized to operatively contact a proximal surface region 640 of the 6-dof sensor 632. The overtube 606 includes the second overtube portion 642 that has a proximal end that defines the second annular flange 644 sized to operatively contact a distal surface region 646 of the 6-dof sensor 632. Thus, the second overtube portion 642 is suspended from the 6-dof sensor 632. It will be appreciated that in other respects the first and second cannulas of FIG. 6A-6B and FIG. 10 are substantially the same.

The foregoing description and drawings of embodiments in accordance with the present invention are merely illustrative of the principles of the invention. Therefore, it will be understood that various modifications can be made to the embodiments by those skilled in the art without departing from the spirit and scope of the invention, which is defined in the appended claims.

The invention claimed is:

1. A cannula comprising:
   a head portion that defines a proximal opening sized to receive one or more surgical instruments;
   an inner tube, having an elongated longitudinal dimension, that depends from and is rigidly fastened to the head portion and that defines a distal opening, wherein the inner tube includes an inner wall that defines an elongated conduit between the proximal opening and the distal opening, wherein the inner wall has a transverse dimension sized to receive the one or more instruments inserted in through the proximal opening and extending through the conduit to the distal opening, and wherein the inner tube includes an outer wall;
   an overtube, having an elongated longitudinal dimension, that is coaxially aligned with the inner tube and that extends about a portion of the inner tube and that depends from and is rigidly fastened to the head portion and that includes an inner wall that is spaced apart from the outer wall of the inner tube, wherein the overtube includes an outer wall; and
   one or more sensors disposed to provide an indication of at least one of a force and a moment applied to the outer wall of the overtube in a direction generally transverse to the longitudinal dimension of the overtube.

2. The cannula of claim 1,
   wherein the one or more sensors are disposed to provide an indication of deflection of at least one of the inner wall and the outer wall of the overtube in a direction generally transverse to the longitudinal dimension of the overtube.

3. The cannula of claim 1,
wherein the one or more sensors are disposed to provide an indication of deflection of the inner wall and the outer wall of the overtube in a direction generally transverse to the longitudinal dimension of the overtube.

4. The cannula of claim 1,
wherein the one or more sensors are disposed to provide an indication of at least one of a force and a moment imparted to the overtube about an axis generally transverse to the longitudinal dimension of the overtube.

5. The cannula of claim 1,
wherein the one or more sensors include at least one sensor disposed on the inner wall of the overtube and at least one sensor disposed on the outer wall of the overtube.

6. The cannula of claim 1,
wherein the one or more sensors include e or more strain gauges.

7. The cannula of claim 1,
wherein the one or more sensors include multiple sensors attached at mu pre cations on one or both of the inner wall and the outer wall of the overtube.

8. The cannula of claim 1,
wherein the one or more sensors includes multiple sensors disposed in a rosette-like pattern.

9. The cannula of claim 1,
wherein the overtube has a stiffness to deflect but not permanently deform under normal human bodywall loads during minimally invasive surgery.

10. The cannula of claim 1,
wherein the overtube has a stiffness to deflect but not permanently deform under loads of approximately 0-50 Newtons.

11. The cannula of claim 1,
wherein the overtube has a stiffness to deflect but not permanently deform under normal human bodywall loads during minimally invasive surgery; and
wherein a gap between the outer wall of the inner tube and the inner wall of the outer tube is large enough that the outer wall of the inner tube does not contact the inner wall of the overtube under normal bodywall loads during minimally invasive surgery.

12. The cannula of claim 1,
wherein the overtube has a stiffness to deflect but not permanently deform under loads of approximately 0-50 Newtons; and
wherein a gap between the outer wall of the inner tube and the inner wall of the outer tube is large enough that the outer wall of the inner tube does not contact the inner wall of the overtube under loads of approximately 0-50 Newtons.

13. The cannula of claim 1,
wherein the outer wall of the overtube has a transverse dimension that is suitable for minimally invasive surgery.

14. The cannula of claim 1,
wherein the outer wall of the overtube has a transverse dimension that is approximately 0.25-1 inches.

15. The cannula of claim 1,
wherein the overtube has a stiffness to deflect but not permanently deform under normal human bodywall loads during minimally invasive surgery;
wherein a gap between the outer wall of the inner tube and the inner wall of the outer tube is large enough that the outer wall of the inner tube does not contact the inner wall of the overtube under normal bodywall loads during minimally invasive surgery; and
wherein the outer wall of the overtube has a transverse dimension that is suitable for minimally invasive surgery.

16. The cannula of claim 1,
wherein the overtube has a stiffness to deflect but not permanently deform under loads of approximately 0-50 Newtons; and
wherein a gap between the outer wall of the inner tube and the inner wall of the outer tube is large enough that the outer wall of the inner tube does not contact the inner wall of the overtube under loads of approximately 0-50 Newtons; and
wherein the outer wall of the overtube has an outer diameter of approximately 0.25-1 inches.

17. The cannula of claim 1,
wherein the overtube comprises stainless steel having a thickness of approximately 0.012-0.030 inches and an outer diameter of approximately 0.25-1 inches inches.

18. The cannula of claim 1,
wherein the inner tube has a greater longitudinal dimension than the overtube.

19. The cannula of claim 1,
wherein the inner tube has and the overtube are substantially cylindrical in contour.

20. A cannula comprising:
a head portion that defines a proximal opening sized to receive one or more surgical instruments;
an inner tube, having an elongated longitudinal dimension, that depends from and is rigidly fastened to the head portion and that defines a distal opening; wherein the inner tube includes an inner wall that defines an elongated conduit between the proximal opening and the distal opening, wherein the inner wall has a transverse dimension sized to receive the one or more instruments inserted in through the proximal opening and extending through the conduit to the distal opening, and wherein the inner tube includes an outer wall;
an overtube having a first portion and a second portion that are coaxially aligned with the inner tube;
one or more sensors interposed between the first portion of the overtube and the second portion of the overtube
wherein the first portion of the of the overtube depends from and is rigidly fastened to the head portion and includes a first inner wall portion that is spaced apart from the outer wall of the inner tube, wherein the first portion of the overtube includes a first outer wall portion;
wherein the second portion of the overtube has an elongated longitudinal dimension and includes a second inner wall portion that is spaced apart from the outer wall of the inner tube,
wherein the second portion of the overtube includes a second outer wall portion wherein the one or more sensors are disposed to provide an indication of a force applied to the second outer wall portion in a direction generally transverse to the longitudinal dimension of the overtube.

* * * * *

UNITED STATES PATENT AND TRADEMARK OFFICE
CERTIFICATE OF CORRECTION

PATENT NO. : 10,470,796 B2
APPLICATION NO. : 15/329982
DATED : November 12, 2019
INVENTOR(S) : Page et al.

Page 1 of 1

It is certified that error appears in the above-identified patent and that said Letters Patent is hereby corrected as shown below:

In the Claims

In Column 11, Line 18, in Claim 6, delete "e" and insert --one-- therefor

In Column 11, Line 22, in Claim 7, delete "mu pre" and insert --multiple-- therefor In Column 11, Line 22, in Claim 7, delete "cations" and insert --locations-- therefor In Column 12, Line 35, in Claim 20, delete "opening;" and insert --opening,-- therefor Signed and Sealed this
Twenty-fourth Day of March, 2020

Andrei Iancu
*Director of the United States Patent and Trademark Office*